United States Patent
Biedermann et al.

(10) Patent No.: US 10,751,090 B2
(45) Date of Patent: Aug. 25, 2020

(54) POLYAXIAL BONE ANCHORING DEVICE AND SYSTEM INCLUDING AN INSTRUMENT AND A POLYAXIAL BONE ANCHORING DEVICE

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 15/669,528

(22) Filed: Aug. 4, 2017

(65) Prior Publication Data

US 2018/0036039 A1    Feb. 8, 2018

Related U.S. Application Data

(60) Provisional application No. 62/371,029, filed on Aug. 4, 2016.

(30) Foreign Application Priority Data

Aug. 4, 2016    (EP) ..................... 16182818

(51) Int. Cl.
*A61B 17/70*    (2006.01)

(52) U.S. Cl.
CPC ........ *A61B 17/7032* (2013.01); *A61B 17/708* (2013.01); *A61B 17/7037* (2013.01);
(Continued)

(58) Field of Classification Search
CPC ........ A61B 17/70–7046; A61B 17/7074–7092
See application file for complete search history.

(56) References Cited

U.S. PATENT DOCUMENTS 5,217,497 A * 6/1993 Mehdian ............ A61B 17/1671
606/268
5,375,956 A    12/1994 Pennig
(Continued)

FOREIGN PATENT DOCUMENTS

JP      2007-506525 A    3/2007
WO   WO 2005/030070 A1  4/2005
(Continued)

OTHER PUBLICATIONS

European Search Report for European Application No. 16182818.1, European Search Report dated Jan. 18, 2017 and dated Jan. 25, 2017 (8 pages).

*Primary Examiner* — Nicholas J Plionis
*Assistant Examiner* — Steven J Cotroneo
(74) *Attorney, Agent, or Firm* — Lewis Roca Rothgerber Christie LLP

(57) ABSTRACT

A bone anchoring device includes a receiving part with a recess for receiving a rod and a flexible head receiving portion for pivotably holding a head of a bone anchoring element, a pressure member configured to exert pressure on the head when the head is held in the head receiving portion, and a clamping ring positionable around the head receiving portion and movable from a first position where the head is pivotable relative to the receiving part, to a second position where the clamping ring exerts a radial force on the head receiving portion to lock the head relative to the receiving part. When the clamping ring is at the first position, the clamping ring abuts the receiving part to restrict upward movement, while a surface of the clamping ring that faces upwards is exposed for engaging an instrument to move the clamping ring to the second position.

23 Claims, 11 Drawing Sheets

(52) U.S. Cl.
CPC ...... *A61B 17/7076* (2013.01); *A61B 17/7083* (2013.01); *A61B 17/7085* (2013.01)

(56) References Cited

U.S. PATENT DOCUMENTS

| | | | |
|---|---|---|---|
| 5,549,608 A * | 8/1996 | Errico | A61B 17/7037 606/264 |
| 5,575,792 A | 11/1996 | Enrico | |
| 5,586,984 A | 12/1996 | Errico | |
| 5,672,176 A | 9/1997 | Biedermann et al. | |
| 5,728,098 A * | 3/1998 | Sherman | A61B 17/7032 606/269 |
| 6,254,602 B1 * | 7/2001 | Justis | A61B 17/7032 606/272 |
| 6,273,888 B1 | 8/2001 | Justis | |
| 6,299,616 B1 | 10/2001 | Beger | |
| 6,582,436 B2 | 6/2003 | Schlapfer et al. | |
| 6,743,231 B1 | 6/2004 | Gray et al. | |
| 7,947,065 B2 | 5/2011 | Hammill, Sr. | |
| 7,955,359 B2 | 6/2011 | Mattis et al. | |
| 7,967,826 B2 | 6/2011 | Colleran et al. | |
| 7,988,694 B2 * | 8/2011 | Barrus | A61B 17/7032 606/246 |
| 8,075,603 B2 | 12/2011 | Hammell, Sr. | |
| 8,298,275 B2 | 10/2012 | Rezach | |
| 8,506,609 B2 * | 8/2013 | Biedermann | A61B 17/7037 606/266 |
| 8,506,610 B2 | 8/2013 | Biedermann | |
| 8,636,781 B2 * | 1/2014 | Biedermann | A61B 17/7032 606/279 |
| 9,005,260 B2 | 4/2015 | Dauster et al. | |
| 9,050,148 B2 * | 6/2015 | Jackson | A61B 17/7038 |
| 9,144,441 B2 | 9/2015 | Biedermann et al. | |
| 9,173,684 B2 * | 11/2015 | Biedermann | A61B 17/7037 |
| 9,333,016 B2 * | 5/2016 | Biedermann | A61B 17/844 |
| 9,456,859 B2 | 10/2016 | Peukert | |
| 9,681,895 B2 | 6/2017 | Biedermann et al. | |
| 9,895,171 B2 * | 2/2018 | Webb | A61B 17/7037 |
| 2004/0254576 A1 | 12/2004 | Dunbar, Jr. et al. | |
| 2005/0080415 A1 * | 4/2005 | Keyer | A61B 17/7037 606/278 |
| 2005/0096653 A1 | 5/2005 | Doubler et al. | |
| 2005/0228385 A1 | 10/2005 | Iott | |
| 2006/0074445 A1 | 4/2006 | Gerber et al. | |
| 2006/0111715 A1 * | 5/2006 | Jackson | A61B 17/861 128/897 |
| 2006/0173454 A1 | 8/2006 | Spitler et al. | |
| 2006/0247658 A1 | 11/2006 | Pond | |
| 2007/0161987 A1 | 7/2007 | Capote | |
| 2007/0270842 A1 | 11/2007 | Bankoski | |
| 2008/0015576 A1 | 1/2008 | Whipple | |
| 2008/0108992 A1 * | 5/2008 | Barry | A61B 17/7037 606/258 |
| 2008/0161859 A1 | 7/2008 | Nilsson | |
| 2009/0036934 A1 * | 2/2009 | Biedermann | A61B 17/7037 606/301 |
| 2009/0062860 A1 | 3/2009 | Frasier | |
| 2009/0105715 A1 | 4/2009 | Belliard | |
| 2009/0105756 A1 | 4/2009 | Richelsoph | |
| 2009/0149887 A1 | 6/2009 | Schlaepfer et al. | |
| 2010/0030135 A1 | 2/2010 | Mitchell | |
| 2010/0131017 A1 | 5/2010 | Farris et al. | |
| 2010/0160977 A1 | 6/2010 | Gephart et al. | |
| 2010/0168800 A1 | 7/2010 | Biedermann et al. | |
| 2010/0204735 A1 | 8/2010 | Gephart et al. | |
| 2011/0060374 A1 | 3/2011 | Sicvol et al. | |
| 2011/0125196 A1 | 5/2011 | Quevedo et al. | |
| 2011/0276098 A1 | 11/2011 | Biedermann et al. | |
| 2012/0046699 A1 | 2/2012 | Jones et al. | |
| 2012/0059426 A1 | 3/2012 | Jackson | |
| 2012/0095516 A1 * | 4/2012 | Dikeman | A61B 17/7032 606/305 |
| 2012/0179209 A1 | 7/2012 | Biedermann et al. | |
| 2012/0179211 A1 * | 7/2012 | Biedermann | A61B 17/7037 606/328 |
| 2012/0203288 A1 | 8/2012 | Lange et al. | |
| 2012/0209332 A1 | 8/2012 | Janowski | |
| 2013/0085536 A1 * | 4/2013 | Biedermann | A61B 17/7076 606/308 |
| 2013/0096623 A1 * | 4/2013 | Biedermann | A61B 17/844 606/279 |
| 2013/0110179 A1 | 5/2013 | Barrus et al. | |
| 2013/0123860 A1 | 5/2013 | Biedermann et al. | |
| 2013/0123861 A1 | 5/2013 | Biedermann et al. | |
| 2014/0031880 A1 | 1/2014 | Biedermann et al. | |
| 2014/0214097 A1 | 7/2014 | Jackson et al. | |
| 2014/0358182 A1 * | 12/2014 | Puekert | A61B 17/7037 606/264 |
| 2015/0119940 A1 * | 4/2015 | Jackson | A61B 17/7076 606/266 |
| 2015/0182265 A1 | 7/2015 | Biedermann et al. | |
| 2016/0030090 A1 | 2/2016 | Webb | |
| 2016/0220281 A1 | 8/2016 | Biedermann et al. | |
| 2017/0020574 A1 | 1/2017 | Biedermann et al. | |

FOREIGN PATENT DOCUMENTS

| | | |
|---|---|---|
| WO | WO 2011/043799 A1 | 4/2011 |
| WO | WO 2011/077511 A1 | 6/2011 |
| WO | WO 2013/050187 A1 | 4/2013 |
| WO | WO 2015/069873 A1 | 5/2015 |

* cited by examiner

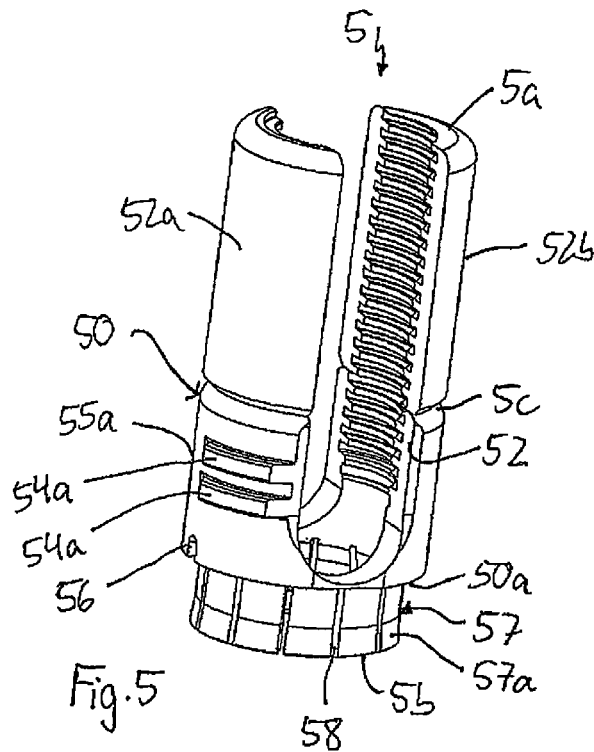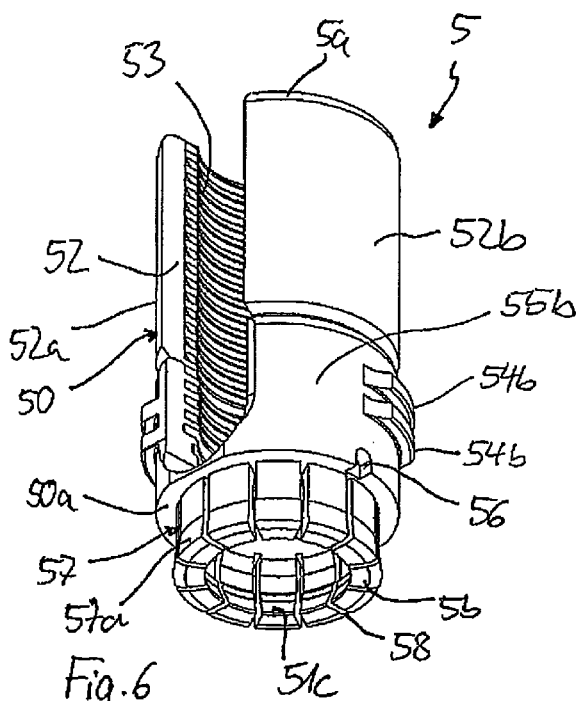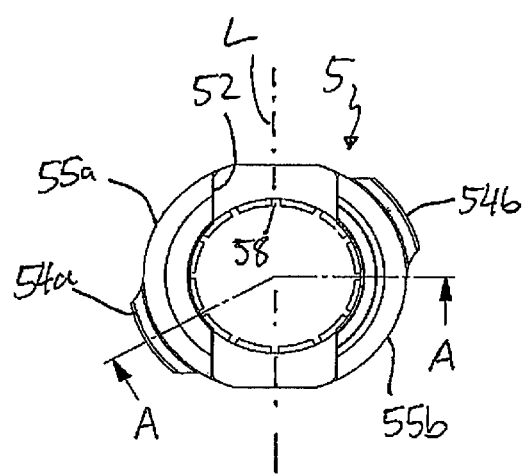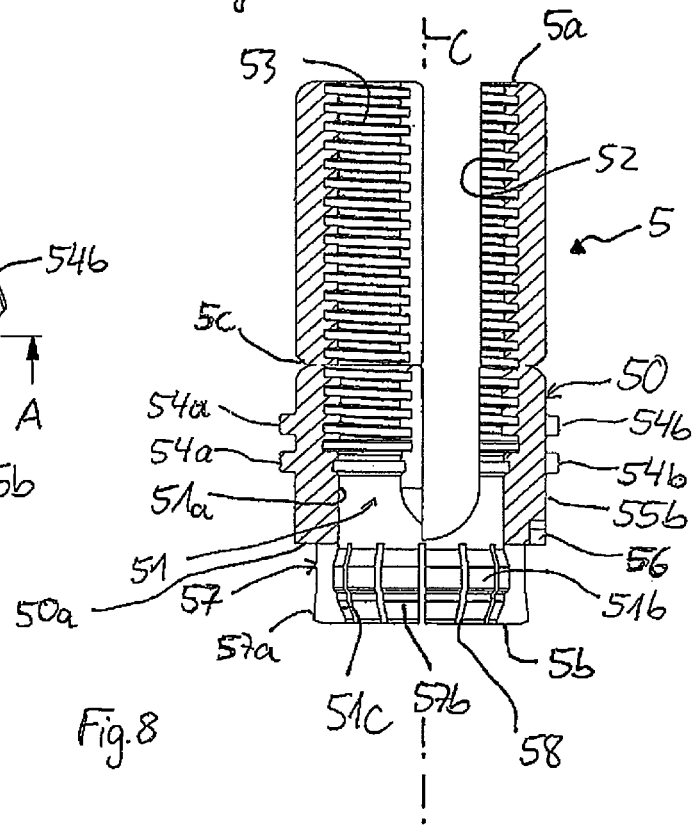

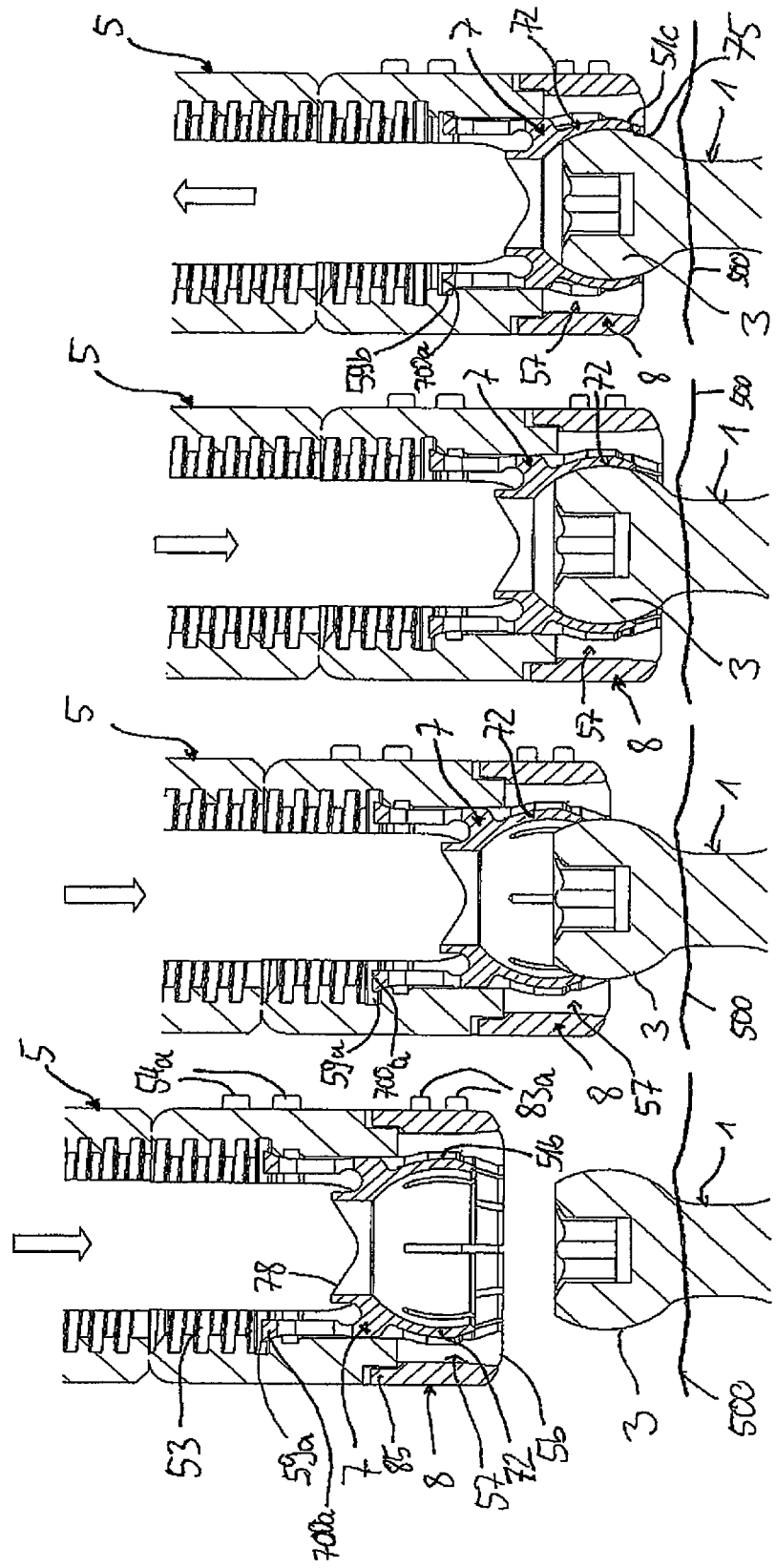

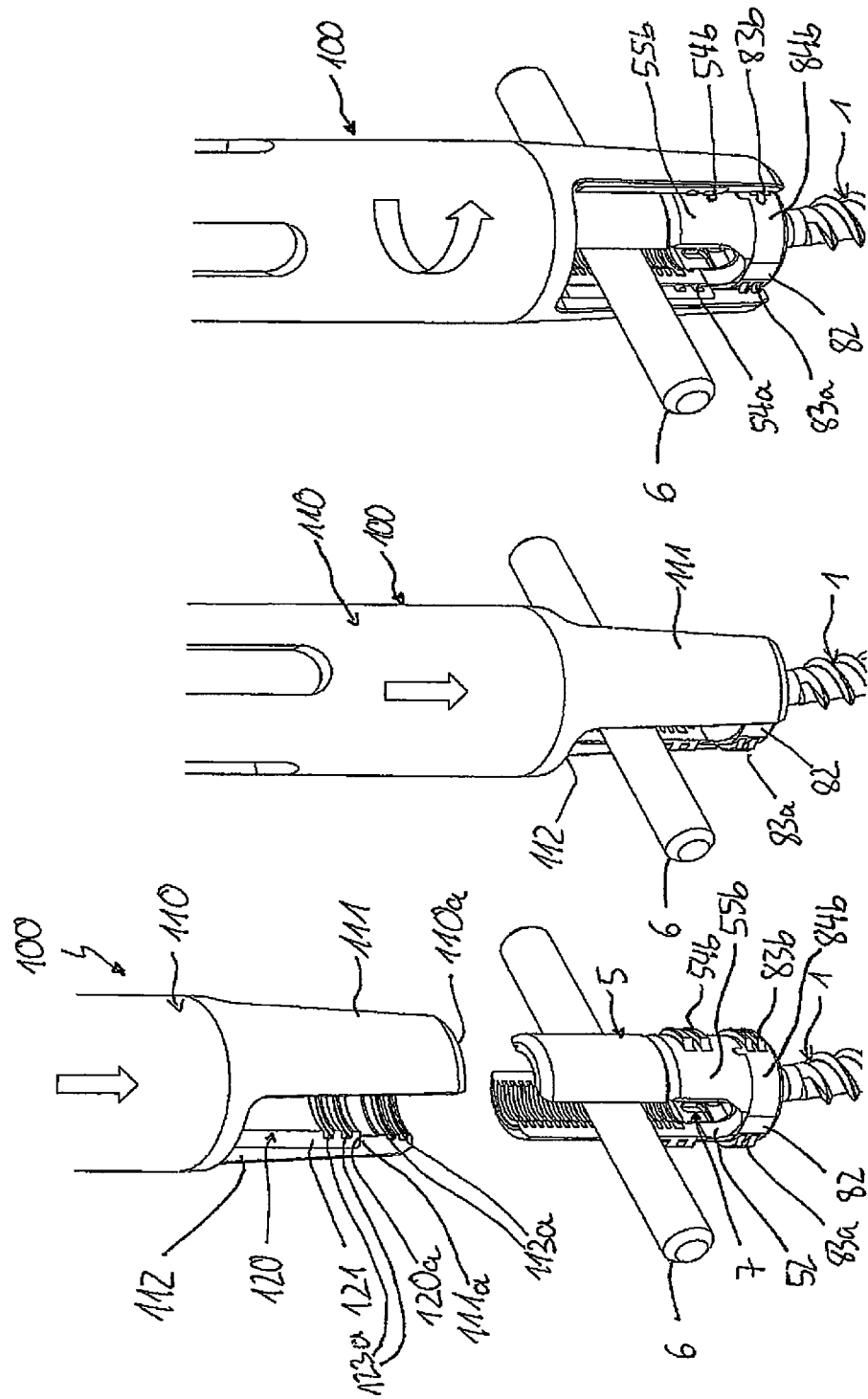

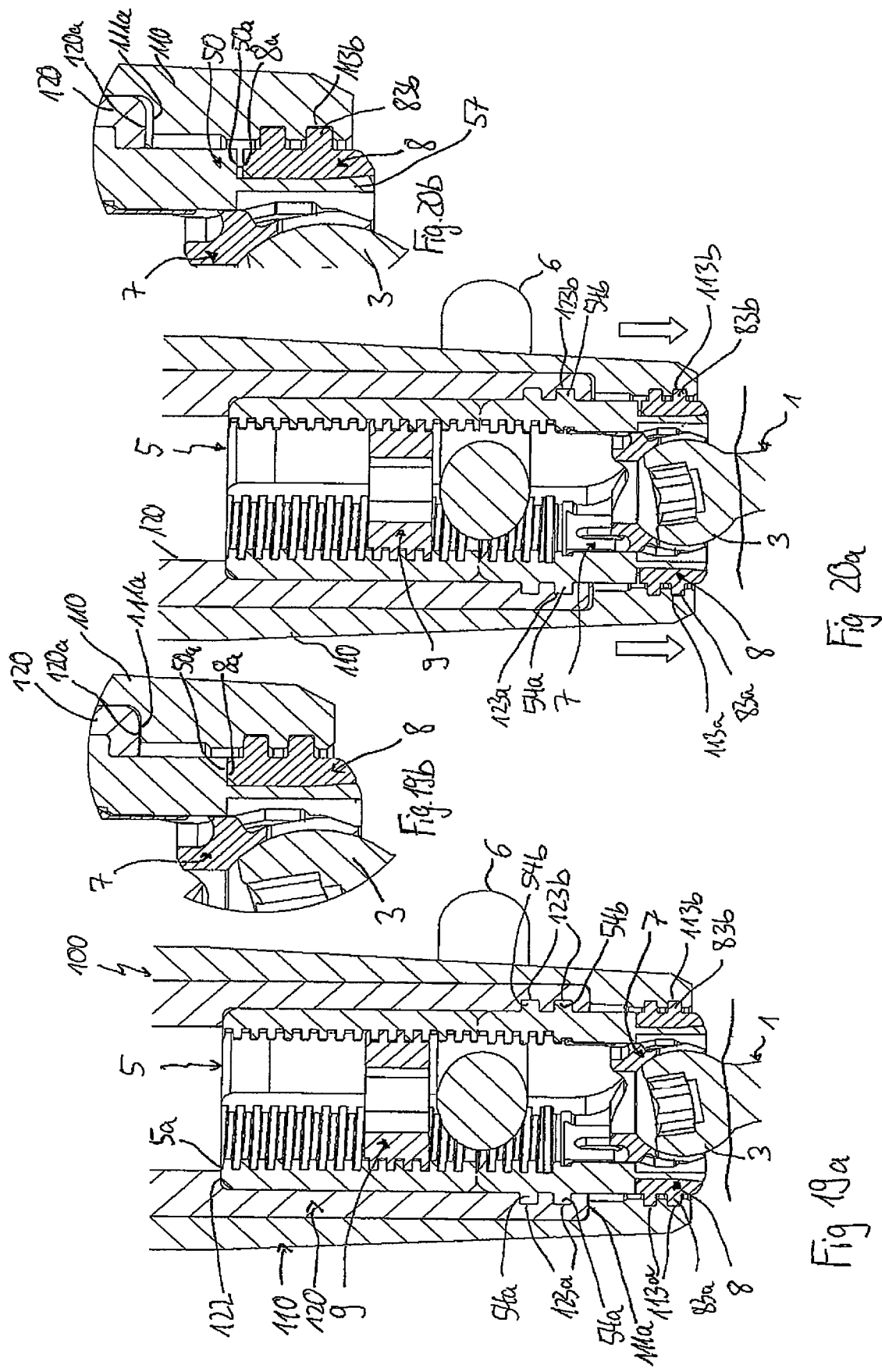

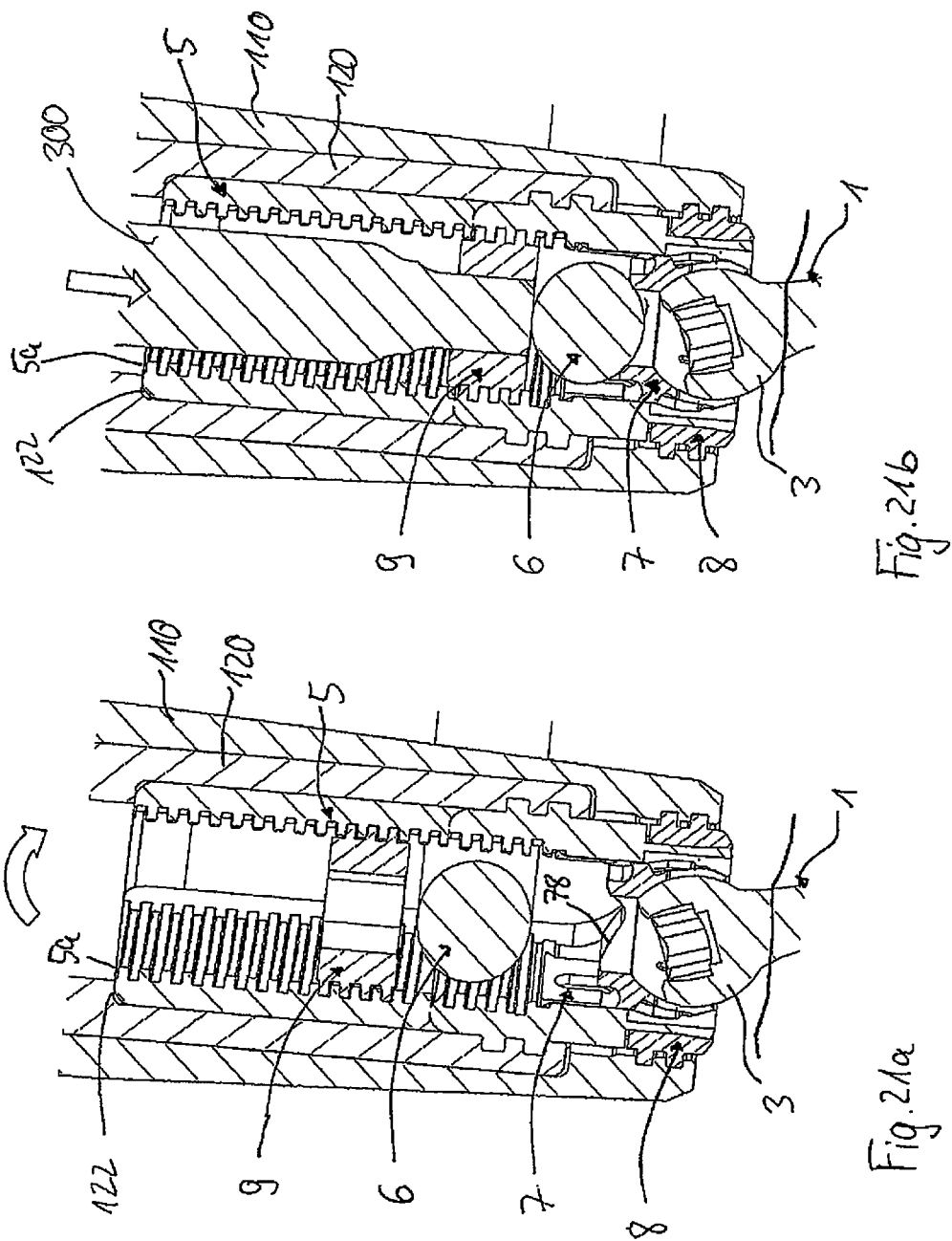

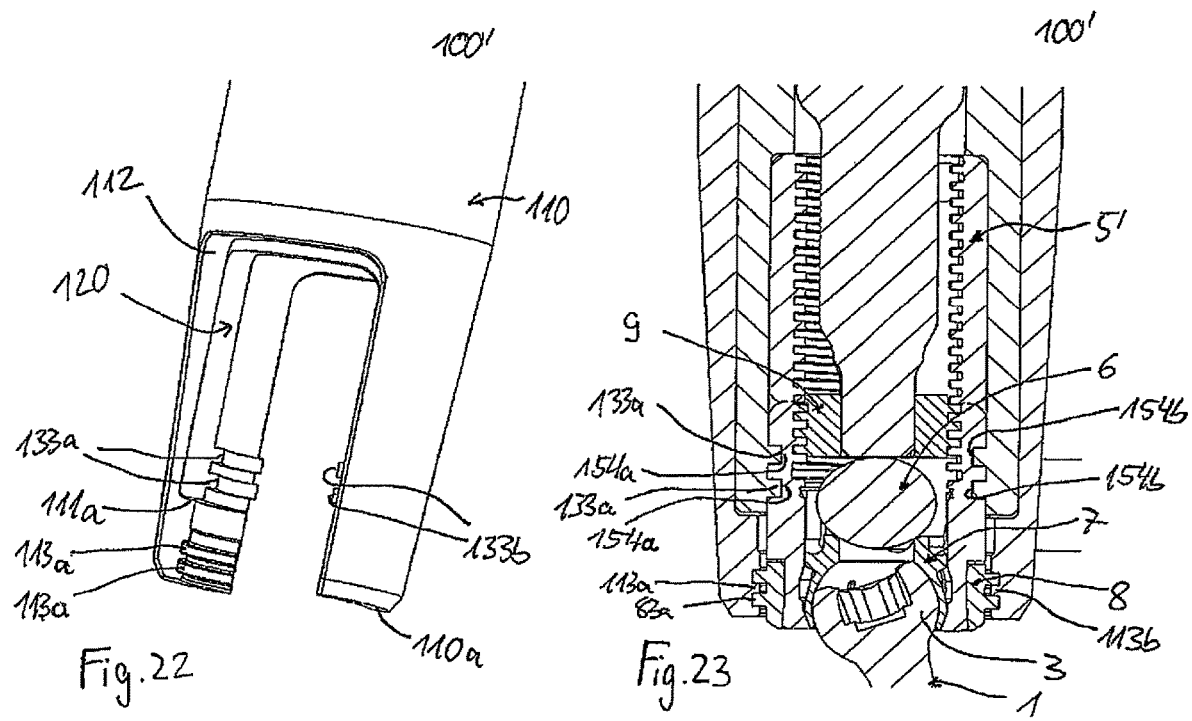
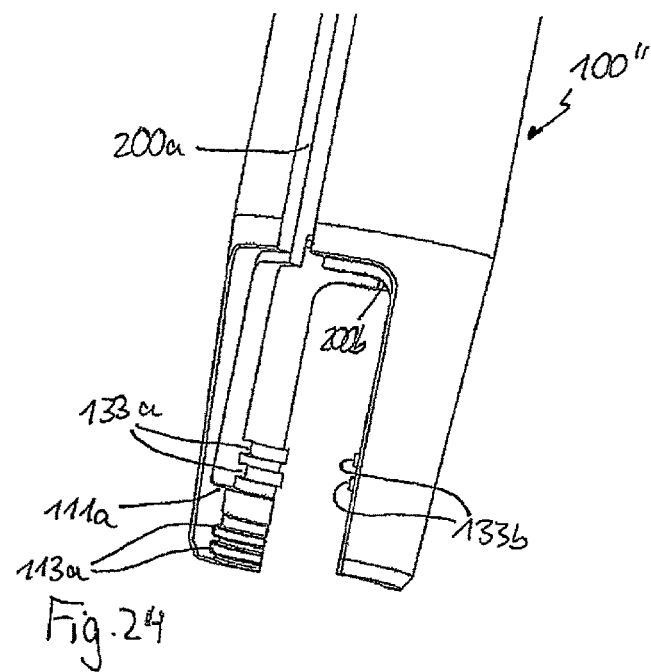

POLYAXIAL BONE ANCHORING DEVICE AND SYSTEM INCLUDING AN INSTRUMENT AND A POLYAXIAL BONE ANCHORING DEVICE

CROSS-REFERENCE TO RELATED APPLICATION(S)

This application claims the benefit of U.S. Provisional Patent Application Ser. No. 62/371,029, filed Aug. 4, 2016, and claims priority from European Patent Application EP 16 182 818.1, filed Aug. 4, 2016, the contents of which are hereby incorporated by reference in their entirety.

BACKGROUND

Field

The invention relates to a polyaxial bone anchoring device and a system including a polyaxial bone anchoring device and an instrument for use with the device. More specifically, the bone anchoring device includes a receiving part for coupling a rod to a bone anchoring element, a pressure member for exerting pressure onto a head of the bone anchoring element and a clamping ring for locking the head and for releasing the lock, for example via the instrument.

Description of Related Art

U.S. Pat. No. 5,672,176 describes an anchoring member for connecting a rod with a bone, including a screw member with a spherical segment-shaped head, a seat part receiving said screw head and said rod, and a pressure member formed to embrace said screw head. The seat part has a portion tapering with a predetermined cone angle, and the pressure member has an outer conical surface with a cone angle corresponding to said predetermined cone angle. The anchoring member can keep the screw head of the screw member locked to the seat part when adjusting the position of the seat part relative to the rod.

US 2013/0085536 A1 describes a polyaxial bone anchoring device including a receiving part with a rod receiving portion and a head receiving portion for introducing and clamping of the head of a bone anchoring element, and a locking ring configured to be arranged around the head receiving portion. The locking ring includes an engagement structure for engagement with a tool to allow the locking ring to be moved out of the locking position, for example, for releasing the locking mechanism. This enables a surgeon or other practitioner to carry out revisions or further positioning or re-positioning of the angular position of a receiving part with respect to the bone anchoring element.

US 2008/0108992 A1 describes a bone fixation device including a receiver having a deformable portion, a bone fastener having a head, the head being insertable into the receiver from the deformable portion, and a retaining member couplable to the deformable portion. The retaining member deforms the deformable portion and angulatably retains the fastener relative to the receiver. The bone fixation device allows a quick loading of the bone fastener from a lower portion of the receiver and still maintains a high degree of angulation similar to the top-loading bone fasteners.

U.S. Pat. No. 7,955,359 B2 describes a bone anchoring device including an anchoring element having a head, a receiving portion for receiving the head and for receiving a rod, a pressure element, and a closure element that acts on the pressure element and on the rod to independently fix the head in the receiving portion and fix the rod in the recess of the receiving part.

SUMMARY

In spinal surgery, often multiple segments of the spinal column have to be corrected and/or stabilized using a spinal rod and polyaxial bone anchoring devices. During such a procedure, repeated adjustments of bone anchoring elements and the rod relative to receiving parts of the polyaxial bone anchoring devices may become necessary.

Embodiments of the invention provide a polyaxial bone anchoring device that allows for improved handling during surgery, and provides an instrument adapted for use with such a polyaxial bone anchoring device.

According to an embodiment, the bone anchoring element can be locked relative to the receiving part at a certain angular position and released again independently from a fixation of the rod. The locking and releasing of the bone anchoring element during surgery using the instrument can also be carried out independently from use of a fixation element, such as a fixation screw, that is used to finally lock the bone anchoring device.

According to one embodiment, the instrument can be used when the rod and the fixation element are already inserted into a channel of the receiving part, but when the rod is not yet fixed. Thus, a temporary locking of the bone anchoring element in the receiving part can be effected with the instrument. As a result, the polyaxial bone anchoring device allows a user to adjust or re-adjust an angular position of the receiving part relative to the bone anchoring element several times while the rod is already inserted.

In the same manner, the rod can be fixed and released independently of locking of the head of the bone anchoring element relative to the receiving part. Therefore, the polyaxial bone anchoring device according to an embodiment may exhibit the same or similar function as a monoaxial bone anchoring device, wherein the axis of the shank of the bone anchoring element is fixed with respect to the receiving part. In one embodiment, the polyaxial bone anchoring device may also exhibit the same or similar function as a polyaxial bone anchoring device with a pressure member and a two-part locking element, wherein the head and the rod can be locked independently.

When the head of the bone anchoring element is locked in the receiving part and the rod is still moveable, it is possible to pull the bone anchoring device with the instrument towards the inserted rod, and thereby also pull the associated vertebrae towards the rod for correcting a position of the vertebrae. With the polyaxial bone anchoring device and the instrument according to an embodiment, various adjustments and re-adjustments of angular position and/or rod position are possible during surgery, without applying large forces that could result in damage to surrounding material, such as tissue, blood vessels, or nerves. Revisions or secondary adjustments of the rod and the receiving part can thus be performed in a more controlled manner.

The polyaxial bone anchoring device according to an embodiment permits insertion of the bone anchoring element first in the bone, and thereafter mounting the receiving part with the clamping ring onto the head of the bone anchoring element. Moreover, with a polyaxial bone anchoring device according to embodiments of the invention, a modular system can be provided that allows for combining of various anchoring elements with the receiving part on demand, depending on the actual clinical requirements. This reduces the overall costs of using polyaxial screws, reduces inventory, and gives the surgeon a wider or more versatile choice of implants.

BRIEF DESCRIPTION OF THE DRAWINGS

Further features and advantages of the invention will become apparent from the description of embodiments by means of the accompanying drawings. In the drawings:

FIG. 5 shows a perspective view from the side of the receiving part of the polyaxial bone anchoring device of FIGS. 1 to 4.

FIG. 6 shows perspective view from the bottom of the receiving part of FIG. 5.

FIG. 7 shows a top view of the receiving part of FIGS. 5 and 6.

FIG. 8 shows a cross-sectional view of the receiving part of FIGS. 5 to 7, the cross-section taken along line A-A in FIG. 7.

FIGS. 17a to 17d show cross-sectional views of steps of mounting the receiving part of the polyaxial bone anchoring device to an anchoring element.

FIGS. 18a to 18c show steps of attaching an instrument to the polyaxial bone anchoring device of FIGS. 1 to 4 according to an embodiment of the invention.

FIG. 19a shows a cross-sectional view of the polyaxial bone anchoring device with the instrument of FIGS. 18a to 18c attached thereto, wherein the clamping ring assumes a first position, and wherein the cross-section is taken in a plane extending through the center of the receiving part and positioned at an angle of about 45° relative to an axis of an inserted rod.

FIG. 19b shows an enlarged view of a detail of FIG. 19a.

FIG. 20a shows a cross-sectional view of the polyaxial bone anchoring device with the instrument of FIGS. 18a to 18c attached thereto, wherein the clamping ring assumes a second position, and wherein the cross-section is taken in a plane extending through the center of the receiving part and positioned at an angle of about 45° relative to an axis of an inserted rod.

FIG. 20b shows an enlarged view of a detail of FIG. 20a.

FIG. 21a and FIG. 21b show steps of use of the polyaxial bone anchoring device with the instrument according to an embodiment of the invention.

FIG. 22 shows a perspective view of a front portion of an instrument according to another embodiment.

FIG. 23 shows a cross-sectional view of another embodiment of the polyaxial bone anchoring device together with the instrument of FIG. 22.

FIG. 24 shows a perspective view of a front portion of a still further embodiment of the instrument.

DETAILED DESCRIPTION

Figure 1:
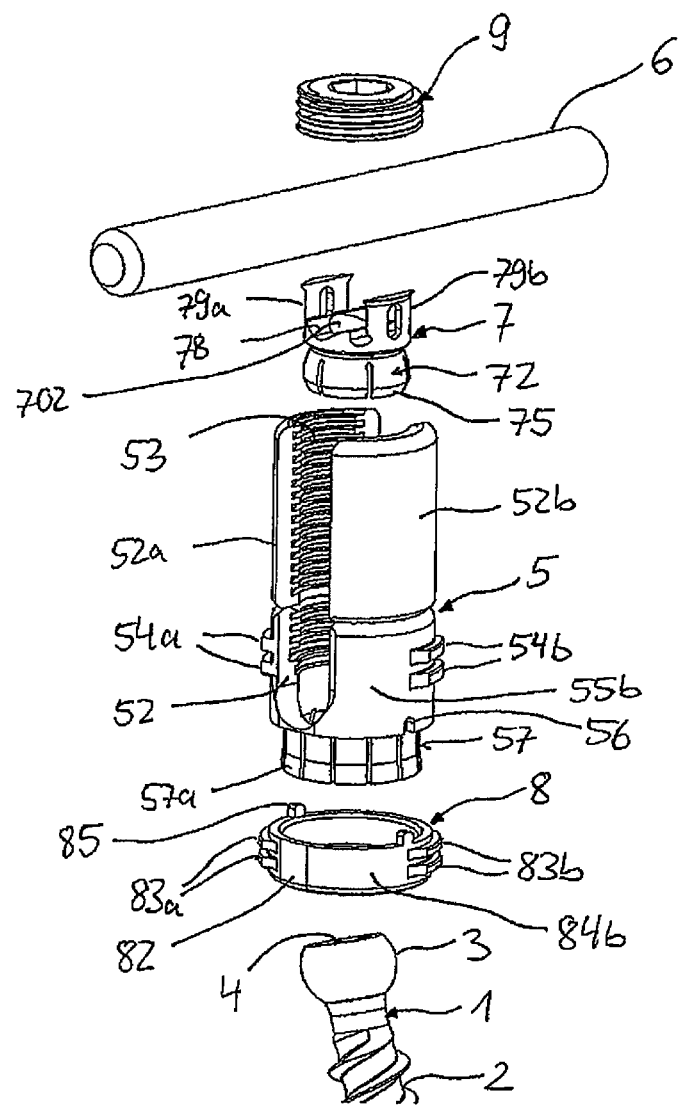
FIG. 1 shows an exploded perspective view of an embodiment of a polyaxial bone anchoring device.

As shown in FIGS. 1 to 4, a bone anchoring device according to an embodiment of the invention includes a bone anchoring element 1 in the form of, for example, a bone screw having a shank 2 with a threaded portion and a head 3 with a spherically-shaped outer surface portion. The head 3 may have a recess 4 for engagement with a driver or tool. The bone anchoring device also includes a receiving part 5 for receiving a rod 6 to be connected to the bone anchoring element 1. Further, a pressure member 7 may be provided in the receiving part 5 for exerting pressure onto the head 3 of the bone anchoring element 1. In addition, the bone anchoring device includes a clamping ring 8 that is mountable to the receiving part 5 for compressing a portion of the receiving part 5, to exert pressure onto the pressure member 7 and in turn onto the head 3. Lastly, the bone anchoring device also includes a fixation element 9 in the form of, for example, an inner screw or set screw for fixing the rod 6 in the receiving part 5.

The receiving part 5 will now be described in greater detail, referring additionally to FIGS. 4 to 8. The receiving part 5 includes first end 5a and an opposite second end 5b, and a central axis C that passes through the first end 5a and the second end 5b. The first end 5a may serve as an abutment for a portion of the instrument, as described in greater detail below. A passage 51 extends through the receiving part 5 from the first end 5a to the second end 5b. The passage 51 may be formed as a cylindrical coaxial bore 51a in a region from the first end 5a to a distance from the first end 5a, and may widen into an accommodation space 51b with a maximum inner diameter that is greater than an inner diameter of the coaxial bore 51a. The accommodation space 51b serves for accommodating head 3 of the bone anchoring element 1 and at least a portion of the pressure member 7. After the section with the maximum inner diameter, the accommodation space 51b narrows in a narrowing portion 51c towards the second end 5b. The narrowing portion 51c can be tapered, more specifically conically tapered, or can narrow in another manner. A substantially U-shaped recess 52 extends from the first end 5a in direction of the second end 5b, wherein a width of the recess 52 is slightly larger than a diameter of the rod 6, such that the rod 6 can be placed in the recess 52 and can be guided therein. The recess 52 forms a channel for the rod 6. By means of the recess 52, two free legs 52a, 52b are formed, on which an internal thread 53 may be provided. The internal thread 53 can be, for example, a metric thread, a flat thread, a negative angle-thread, a saw-tooth thread or any other thread form. Meanwhile, the fixation element 9 in the form of an inner screw has a thread corresponding to the internal thread 53 provided on the legs 52a, 52b. Preferably, a thread form such as a flat thread or a negative angle thread is used to prevent or reduce splaying of the legs 52a, 52b when the fixation element 9 is screwed-in.

At a distance from the first end 5a, a circumferential groove 5c is provided that permits breaking off of a portion of the legs 52a, 52b above the groove 5c. Hence, the upper portions of the legs 52a, 52b form extended tabs. The depth of the recess 52 is such that when the rod 6 is placed into the recess 52 and the fixation element 9 is screwed between the legs 52a, 52b, the fixation element 9 does not substantially protrude out the receiving part 5 after the extended tabs have been broken off.

An upper part 50 of the receiving part 5 which is adjacent to the first end 5a has a substantially cylindrical outer surface. At an outer surface of the upper part 50 of the receiving part 5, an engagement structure for engagement with the instrument is provided, wherein the engagement structure may be formed by a plurality of circumferential ribs 54a, 54b. In the embodiment shown, on each leg 52a, 52b, two ribs 54a, 54b are respectively provided. The ribs 54a, 54b are positioned between the groove 5c and a lower end 50a of the upper part 50. Each of the plurality of ribs 54a, 54b extends over a segment of the circumference of the upper part 50, for example, for approximately a quarter circle (see FIGS. 5 and 7). The arrangement is such that one end of each rib 54a, 54b is positioned at the recess 52 and the other end of each rib extends approximately to the middle of each leg 52a, 52b. Hence, in a circumferential direction, there is a rib-free surface portion 55a, 55b on the outer surface of each leg 52a, 52b. Furthermore, the ribs 54a, 54b are arranged in an asymmetric manner with respect to a plane extending through the central axis C and a longitudinal axis L of the recess 52. More specifically, the positions of the ribs 54a, 54b are offset from one another by 180° measured in relation to the central axis C, and are rotated with respect to the central axis C such that the ribs 54a of the leg 52a extend to the rod receiving recess 52 at one side of the receiving part 5 and the ribs 54b extend to the rod receiving recess 52 at the other side of the receiving part 5. This permits the instrument to be placed first onto the rib-free portions 55a, 55b, and then to be rotated to engage the ribs 54a, 54b, as described in greater detail below. The ribs 54a, 54b may have a substantially rectangular cross-section and may have inclined end portions in the circumferential direction. It shall be understood that the number of ribs on each leg 52a, 52b is not limited to two, and that one single rib or more than two ribs may instead be provided on each leg in other embodiments. Also the shape of the ribs may be different in other embodiments.

Figure 4:
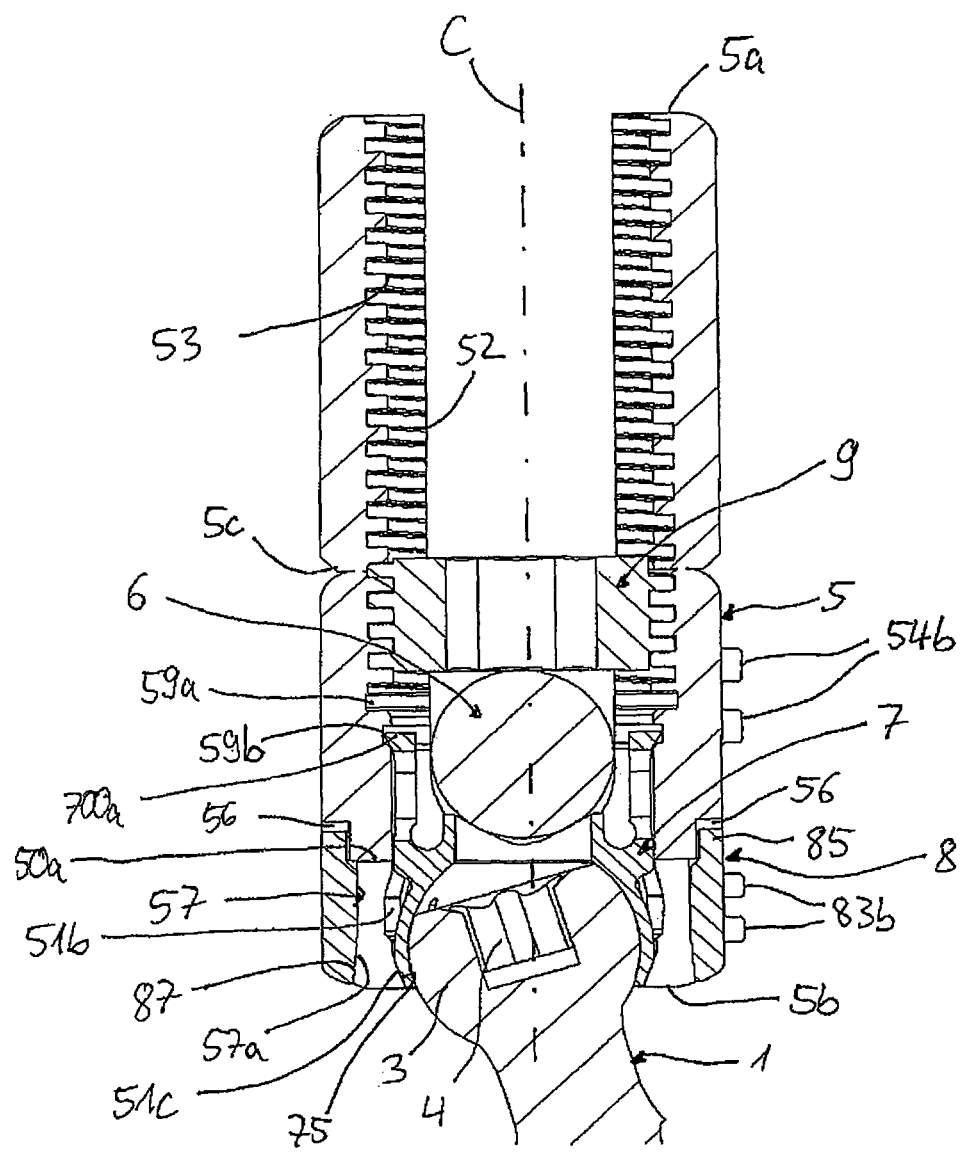
FIG. 4 shows an enlarged cross-sectional view of the polyaxial bone anchoring device of FIGS. 1 to 3, wherein the cross-section has been taken in a plane perpendicular to an axis of an inserted rod and extending through the center of a receiving part of the bone anchoring device.
Figure 9:
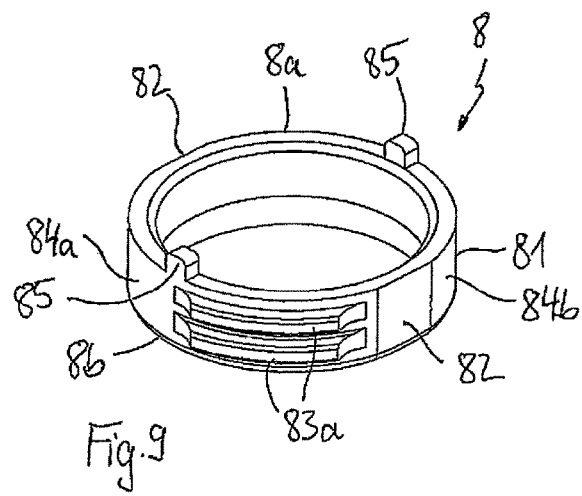
FIG. 9 shows a perspective view of a clamping ring of the polyaxial bone anchoring device of FIGS. 1 to 4.
Figure 10:
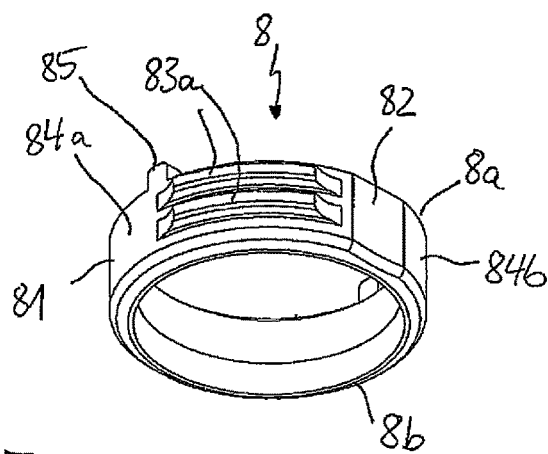
FIG. 10 shows a perspective view from the bottom of the clamping ring of FIG. 9.
Figure 11:
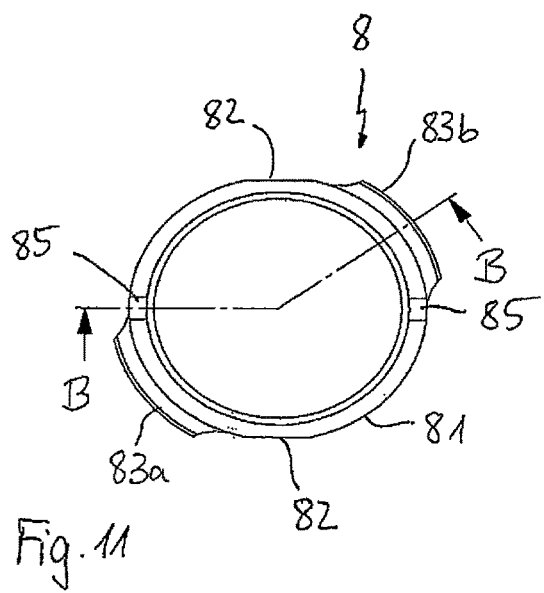
FIG. 11 shows a top view of the clamping ring of FIGS. 9 and 10.
Figure 12:
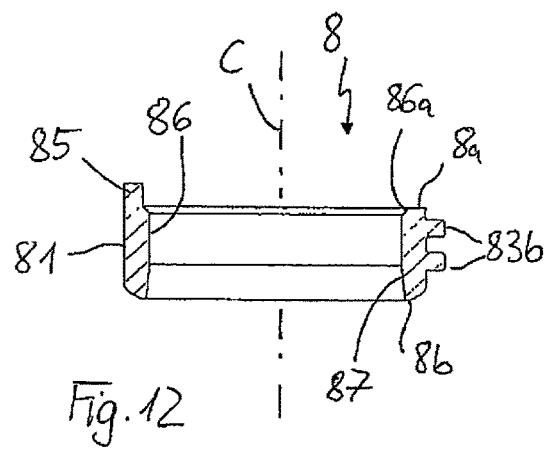
FIG. 12 shows a cross-sectional view of the clamping ring of FIGS. 9 to 11, the cross-section taken along line B-B in FIG. 11.
Figure 13:
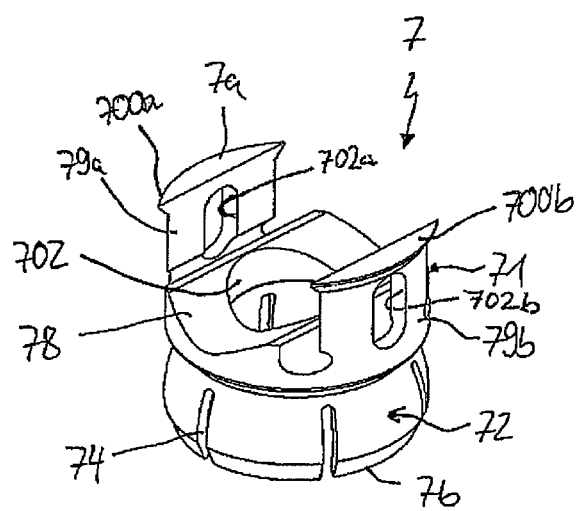
FIG. 13 shows a perspective view from the top of a pressure member of the polyaxial bone anchoring device of FIGS. 1 to 4.
Figure 14:
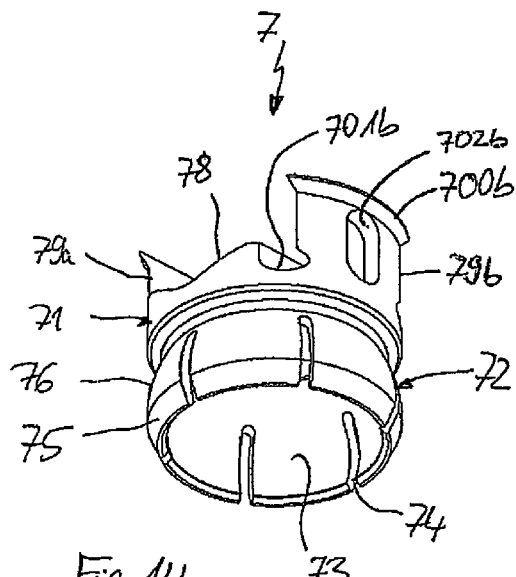
FIG. 14 shows a perspective view from the bottom of the pressure member of FIG. 13.
Figure 15:
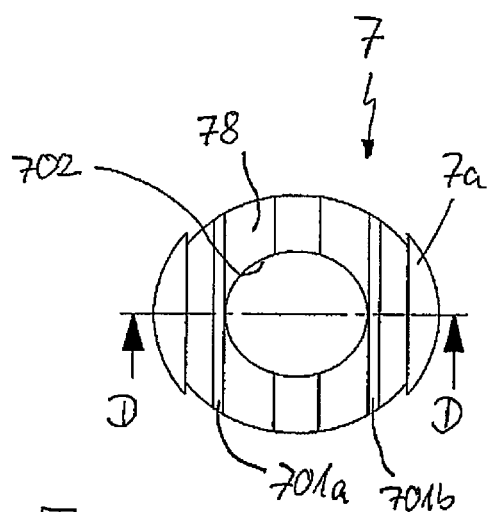
FIG. 15 shows a top view of the pressure member of FIGS. 13 and 14.
Figure 16:
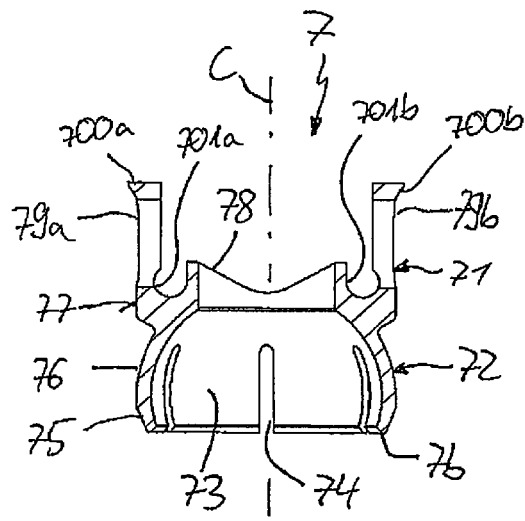
FIG. 16 shows a cross-sectional view of the pressure member of FIGS. 13 to 15, the cross-section taken along line D-D in FIG. 15.

As shown in more detail in FIGS. 4 and 8, on the inner wall of the passage 51 in the upper part 50, two stops are provided for the pressure member 7. A first stop is formed by the last thread turn of the internal thread 53, above an undercut 59a positioned at the lower end of the thread 53. The first stop prevents upward movement of the pressure member 7 when the head 3 is inserted into the receiving part 5. A second stop is formed by a circumferential groove 59b that is positioned at a distance from the first stop in a direction toward the lower end 50a. The second stop prevents upward movement of the pressure member 7 when the pressure member 7 is at a lower position.

At the lower end 50a of the upper part 50 of the receiving part 5, two recesses 56 open towards the lower end 50a and are positioned in a circumferential direction at approximately 90° from the center of the U-shaped recess 52. The recesses 56 have a small width in the circumferential direction, and may have substantially straight sidewalls and a curved closed end. The recesses 56 serve for engagement with corresponding projections of the clamping ring 8.

Between the upper part 50 and the second end 5b, a head receiving portion 57 of the receiving part 5 is provided. The head receiving portion 57 has a substantially cylindrical outer surface, with a smaller diameter than the diameter of the upper part 50 of the receiving part 5. Adjacent the second end 5b, there is a portion 57a of the outer surface that slightly tapers outwards. The head receiving portion 57 includes the accommodation space 51b. To allow insertion of the head 3, the head receiving portion 57 is flexible. In the embodiment shown, the head receiving portion 57 includes a plurality of flexible wall sections 57b that are separated by slits 58 that extend in a longitudinal direction and that are open towards the second end 5b. The number and size of the slits 58 is provided depending on the desired flexibility of the head receiving portion 57. An inner diameter of the passage 51 at the second end 5b is such that the head 3 can be inserted from the second end 5b. The inner diameter of the passage 51 at the second end 5b may be slightly smaller than a greatest outer diameter of the head 3, so that the head receiving portion 57 may be expanded slightly when the head 3 is inserted.

The clamping ring 8 will now be described in greater detail, referring additionally to FIGS. 9 to 12. The clamping ring 8 includes an upper end or first end 8a and an opposite lower end or second end 8b, and may have a substantially cylindrical outer surface 81. The outer diameter of the cylindrical surface 81 may be such that when the clamping ring 8 is mounted around the head receiving portion 57 of the receiving part 5, the outer cylindrical surface 81 of the clamping ring 8 and the outer cylindrical surface of the upper part 50 of the receiving part 5 are flush with each other as depicted, for example, in FIGS. 2 to 4. An inner diameter of the clamping ring 8 is such that the clamping ring 8 can be mounted around the head receiving portion 57, wherein the upper end 8a faces towards the lower end 50a of the upper part 50 of the receiving part 5. Alignment features in the form of flat portions 82 are provided at the outer surface 81 of the clamping ring 8. The flat portions 82 are offset by 180° and may have a substantially rectangular contour. The alignment features provide a reference for aligning the clamping ring 8 correctly with respect to the receiving part 5, in particular with respect to the ribs 54a, 54b.

The clamping ring 8 further includes on its outer surface 81 an engagement structure for engagement with the instrument. The engagement structure includes a plurality of ribs 83a, 83b that are arranged on the outer surface 81 of the clamping ring 8. The ribs 83a, 83b extend over a segment of an outer circumference of the clamping ring 8, for example, for approximately a quarter circle or less than a quarter circle. In the embodiment shown, the ribs include two pairs 83a, 83b of ribs that are arranged diametrically opposite to one another. Each pair 83a, 83b includes two axially spaced apart ribs extending in a circumferential direction on each side of the clamping ring 8. The position of the ribs 83a, 83b in a circumferential direction corresponds to the position of the ribs 54a, 54b of the receiving part 5 when the clamping ring 8 is mounted around the head receiving portion 57 and when the flat portions 82 of the clamping ring 8 are aligned with the U-shaped recess 52 of the receiving part 5. In other words, one group of ribs 83a extends circumferentially around the clamping ring 8, from a circumferential position substantially adjacent to one flat portion 82 to a certain distance therefrom, and the opposite group of ribs 83b extends circumferentially from a position substantially adjacent to the opposite flat portion 82 to a certain distance therefrom. By means of this, rib-free surfaces 84a, 84b are formed between the ribs 83a, 83b that are aligned with the rib-free surfaces 55a, 55b of the receiving part 5 when the clamping ring 8 is mounted around the head receiving portion 57. The ribs 83a, 83b may have substantially rectangular cross-sections and inclined end portions in a circumferential direction. It shall be noted, however, that the shape of the ribs may be different in other embodiments. Also, in other embodiments, there may be one single rib or more than two ribs on each side of the clamping ring 8.

Figure 2:
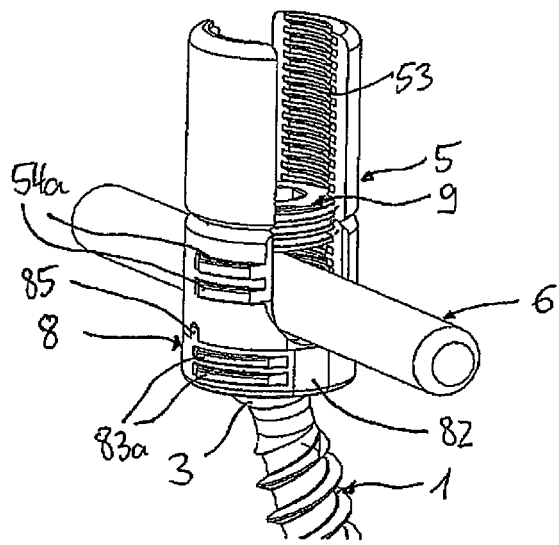
FIG. 2 shows a perspective view of the polyaxial bone anchoring device of FIG. 1 in an as-assembled state.
Figure 3:
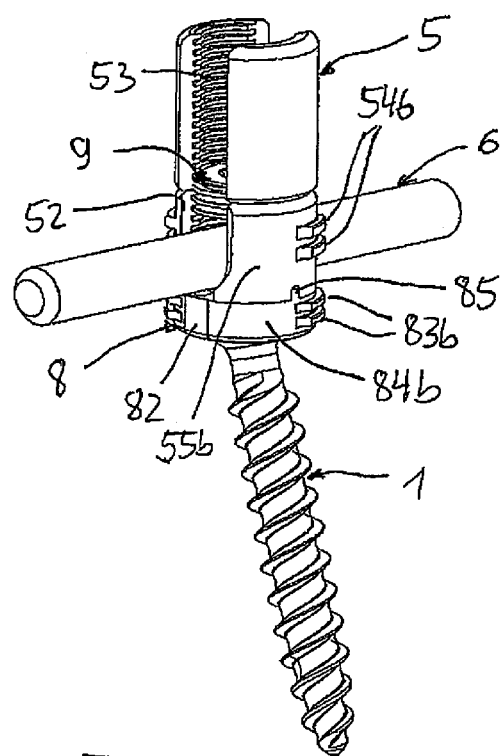
FIG. 3 shows a further perspective view of the polyaxial bone anchoring device of FIG. 1 in an assembled state.

At the upper end 8a, two opposite projections 85 are provided that project upward from the upper end 8a towards upper part 50 of the receiving part 5 when the clamping ring 8 is mounted to the receiving part 5. The projections 85 have a shape that substantially fits into the recesses 56 at the lower end of the upper part 50 of the receiving part 5. As depicted in FIGS. 2 and 3, the projections 85 are at circumferential positions substantially at the respective end of the ribs that are farther away from the flat portions 82. The projections 85 may have such a height that the clamping ring 8 is secured against rotation around the receiving part 5 in both its upper and lower axial positions.

As can be seen in particular in FIGS. 9 to 12, clamping ring 8 further has a first inner cylindrical surface portion 86 that is adjacent or substantially adjacent to the upper end 8a. There may be a small inclined surface or beveled surface 86a provided adjacent to the upper end 8a to facilitate mounting of the clamping ring 8 to the receiving part 5. Adjacent or substantially adjacent to the lower end 8b, an inner surface 87 of the clamping ring 8 may be tapered in a manner such that the inner diameter conically widens towards the lower end 8b. The inner surface 87 is configured to cooperate with the outer surface portion 57a of the head receiving portion 57 in a manner such that when the clamping ring 8 is moved towards a lowermost position on the head receiving portion 57, the cooperating surfaces 57a of the head receiving portion 57 and 87 of the clamping ring 8 exert an increasing inwardly directed radial force towards the pressure member 7 and the head 3. Moreover, a height of the clamping ring 8 in an axial direction, as can be seen in FIGS. 2 and 3, corresponds substantially to a height of the head receiving portion 57 of the receiving part 5.

The pressure member 7 will now be described in greater detail, by referring additionally to FIGS. 13 to 16. The pressure member 7 includes an upper or first portion 71 with an upper end 7a and a lower or second portion 72 with a lower end 7b. The second portion 72 has a hollow interior 73 that may be substantially spherically-shaped to clamp the spherical head 3 therein. The flexible portion 72 is open at the second end 7b. A plurality of slits 74 extend from the lower end 7b through the second portion 72. The number and dimensions of the slits 74 are such that the wall of the second portion 72 is flexible enough to snap onto the head 3 when the head 3 is being inserted into the hollow interior 73. An outer surface portion 75 adjacent to the lower end 7b of the pressure member 7 may be tapered, in particular conically tapered. The outer surface portion 75 is configured to cooperate with the inner surface portion 51c of the receiving part 5 that is provided adjacent to the lower end 5b of the receiving part 5. It shall be understood that in other embodiments, the outer surface portion 75 may narrow in another manner towards the lower end 7b. Another outer surface portion 76 of the second portion 72 of the pressure member may be spherical segment-shaped as shown in the embodiment, so that the second portion is cap-like. It shall be noted that in other embodiments, the outer surface can have any other shape, such as tapered or cylindrical or combinations of tapered, cylindrical and spherical.

The first portion 71 of the pressure member 7 may have a substantially cylindrical outer surface 77 adjacent to the second portion 72. In the embodiment shown, the second portion 72 is recessed with respect to the cylindrical portion 77. In other embodiments, however, any other shape may be possible for the portion 77. A rod support surface 78 may be provided in the first portion 71 that is configured to support an inserted rod 6. The rod support surface 78 may have a V-shaped cross-section in a direction transverse to the central axis C to permit support of rods of different diameter, but can also be flat or cylindrical or otherwise shaped.

The longitudinal axis of the rod support surface 78 extends transverse to the central axis C. To the left and to the right of the rod support surface 78, upstanding legs 79a, 79b are formed that have a substantially flat inner surface and a substantially cylindrical outer surface. The upstanding legs 79a, 79b have outwardly directed portions 700a, 700b at their free ends, respectively. The outwardly directed portions 700a, 700b are configured to engage the grooves 59a, 59b when the pressure member is in an insertion position and in a clamping position of the head 3, respectively. Between the rod support surface 78 and the upstanding legs 79a, 79b, grooves 701a, 701b extending parallel to the rod support surface 78 are formed that render the upstanding legs 79a, 79b more flexible. The grooves 701a, 701b may have a circular segment-shaped cross-section. At the center of the upstanding legs 79a, 79b, elongate through-holes 702a, 702b may be provided, the longitudinal axes of which are parallel to the central axis C. The through-holes 702a, 702b may be adapted to be engaged by pins (not shown) or other holding means to hold the pressure member 7 inside the receiving part 5. To allow access to the head 3 with a driver or tool, a coaxial bore 702 is provided in the pressure member 7.

The dimensions of the pressure member 7 are such that the second portion 72 can expand in the accommodation space 51b when the head 3 of the bone anchoring element 1 is inserted therein. An outer diameter of the cylindrical portion 77 is slightly smaller than an inner diameter of the passage 51 in the upper part 50 of the receiving part 5, such that the pressure member 7 can slide therein. The pressure member 7 may be insertable from the upper end 5a of the receiving part 5, whereby during insertion the flexible second portion 72 may be slightly compressed and the upstanding legs 79a, 79b may also be slightly compressed towards each other until the second portion 72 is arranged in the accommodation space 51b and the outwardly directed portions 700a, 700b engage the groove 59a in the receiving part 5.

The receiving part 5, the pressure member 7, the clamping ring 8, and the bone anchoring element 1, as well as the rod 6, may each be made of bio-compatible materials, for example, of titanium or stainless steel, of a bio-compatible alloy, such as NiTi-alloys, for example Nitinol, of magnesium or magnesium alloys, or from a bio-compatible plastic material, such as, for example, polyether ether ketone (PEEK) or poly-1-lactide acid (PLLA). In addition, the parts can be made of the same material, or can be made of different materials from one another.

Turning now to FIGS. 17a to 17d, a use of the polyaxial bone anchoring device will be explained. First, as illustrated in FIG. 17a, the bone anchoring element 1 may already be inserted into a bone 500 before the receiving part 5 with the pressure member 7 and the clamping ring 8 is mounted thereon. The pressure member 7 is in the receiving part 5 in an insertion position where the head 3 can be inserted. The outwardly directed portions 700a, 700b extend into the first groove 59a at the receiving part 5, such that the last turn of the internal thread 53 forms a stop for the pressure member 7. The second portion 72 of the pressure member 7 extends substantially into the accommodation space 51b. The clamping ring 8 is in an upper position in which the projections 85 engage the recesses 56 and the upper end 8a abuts against the lower end 50a of the upper part 50 of the receiving part 5. Thus, the clamping ring 8 is correctly aligned and secured against rotation relative to the receiving part 5.

As further illustrated in FIG. 17b, the head 3 of the bone anchoring element enters the head receiving portion 57 of the receiving part 5 through the passage at the lower end 5b. The receiving part 5 is then further moved down, as can be seen in FIG. 17c. Simultaneously, the head 3 enters the hollow interior 73 of the second portion 72 of the pressure member 7. The pressure member 7 is prevented from escaping through the first end 5a of the receiving part 5 by the stop provided by the last turn of the internal thread 53. Since the second portion 72 of the pressure member 7 is flexible, it can expand in the accommodation space 51b when the head 3 is inserted, and snaps over the head 3.

Finally, as depicted in FIG. 17d, the receiving part 5 is pulled upward with respect to the bone anchoring element 1 and the pressure member 7. Thereby, the upstanding legs 79a, 79b snap with their outwardly directed portions 700a, 700b into the groove 59b. At the same time, the head 3 and the pressure member 7 are pulled into the narrowing portion 51c of the receiving part. The inner surface 51c and the outer surface 75 of the pressure member 7 generate an increasing pressure onto the head 3. This frictional clamping of the head 3 in the receiving part 5 may be such that the head 3 can be pivoted in the receiving part 5 by overcoming the frictional force. Depending on the strength of the frictional force, the receiving part may be temporarily held at a specific angular position relative to the bone anchoring element 1. At the same time, the head 3 is prevented from being pulled out of the receiving part 5.

Turning now to FIGS. 18a to 18c, first, an instrument that is adapted for use with the polyaxial bone anchoring device will be described. The instrument 100 includes an outer tube 110 and an inner tube 120, wherein the outer tube 110 and the inner tube 120 are axially displaceable relative to each other along a longitudinal axis of the tubes. The outer tube 110 and the inner tube 120 may be secured against rotation relative to each other, so that rotating the outer tube 110 also rotates the inner tube 120 and vice-versa. The axial position of the inner tube 110 relative to the outer tube 120 may be locked. The displacement of the inner tube 110 and the outer tube 120 relative to each other may be effected, for example, by a lever (not shown), such as a toggle lever, whereby a first end of a first lever arm is connected to the outer tube 110 and a first end of a second lever arm is connected to the inner tube 120, and where second ends of the lever arms can be actuated by hand. This is, however, only an example, and any other mechanism for displacing and locking the tubes 110, 120 relative to each other can also be implemented.

The outer tube 110 and the inner tube 120 each has a respective front portion 111, 121. An outer surface of the front portion 111 of the outer tube 110 may be slightly tapered towards a free end 110a of the outer tube 110. At least the front portion 121 of the inner tube 120 may be guided in the front portion 111 of the outer tube 110. A free end 120a of the inner tube 120 may abut against a circumferentially extending shoulder 111a on an inner wall of the outer tube 110. Further, a recess 112 is formed that extends from the free end 110a of the outer tube 110, and through the front portion 111 of the outer tube 110 and the front portion 121 of the inner tube 120. The recess 112 has an inner diameter or width that is at least as large as an outer diameter of the receiving part 5 in the region of the rib-free surfaces 55a, 55b, such that the instrument 100 can be placed onto and around the receiving part 5 and the clamping ring 8. A length of the recess 112 in an axial direction is such that the receiving part 5 can be accommodated in the front portion 111, 121 of the tubes 110, 120 of the instrument 100. Thus, the inserted rod 6 can also extend through the recess 112. At a distance from the free end 120a of the inner tube 120, an inner shoulder 122, for example an annular shoulder, is formed, which serves as an abutment for the first end 5a of the receiving part 5, as depicted in FIGS. 19a and 20a. By means of the recess 112, two free legs are formed on the instrument 100. The shape of the recess 112 is such that the width of the legs may decrease towards the free end 110a. This facilitates easier finding of the receiving part 5 in-situ and placing of the instrument 100 onto the receiving part 5 in-situ during surgery.

At a distance from the free end 110a, the outer tube 110 defines circumferentially extending grooves 113a, 113b in an inner wall of the legs, respectively. The number and shape of the grooves 113a, 113b respectively corresponds to the number and shape of the ribs 83a, 83b of the clamping ring 8. In the embodiment shown, two axially spaced apart grooves 113a, 113b are provided on each side. The grooves 113a, 113b are configured to engage the ribs 83a, 83b of the clamping ring 8. Similarly, circumferentially extending grooves 123a, 123b are provided at an inner wall of the inner tube 120 at a distance from the free end 120a. The grooves 123a, 123b are configured to cooperate with the ribs 54a, 54b of the receiving part 5. When the inner tube 120 is at an engagement position of the instrument 100, described in greater detail below, the distance between the grooves 113a, 113b of the outer tube 110 and the grooves 123a, 123b of the inner tube 120 corresponds to the distance between the ribs 83a, 83b on the clamping ring 8 and the ribs 54a, 54b on the receiving part 5 when the clamping ring 8 is at the upper position as depicted in FIG. 18a.

The instrument 100 as a whole, or parts thereof, may be made of one or more of the same materials mentioned above with respect to the polyaxial bone anchoring device.

The operation of the instrument 100 is as follows. First, as illustrated in FIGS. 18a to 18c, the steps of placing the instrument 100 onto the receiving part 5 are illustrated. In FIG. 18a, the bone anchoring element 1 may already be inserted into a bone. The clamping ring 8 is in the upper position and the projections 85 engage the recesses 56 of the upper part 50 of the receiving part 5. The rod 6 and a fixation element 9 may already be inserted in the receiving part 5, but the fixation element 9 is not tightened so that the rod 6 is still movable along the rod axis, and may also have some space for moving axially up and down relative to the receiving part 5. The front portion of the instrument 100 is oriented such that the legs of the instrument 100 are aligned with the rib-free surface portion 55a, 55b of the receiving part 5 and the rib-free surface portions 84a, 84b of the clamping ring 8. Then, as depicted in FIG. 18b, the instrument 100 is moved downward relative to the receiving part 5 so that the legs of the instrument 100 are placed over the receiving part 5 until the first end 5a of the receiving part abuts against the inner shoulder 122 of the inner tube 120 (depicted in FIGS. 19a and 20a). In this position the grooves 113a, 113b of the outer tube 110 are at a same axial position as the ribs 83a, 83b of the clamping ring 8, and the inner grooves 123a, 123b of the inner tube 120 are at a same axial position as the ribs 54a, 54b of the receiving part 5. Therefore, when the instrument 100 is rotated, the grooves 113a, 113b of the outer tube 110 engage the ribs 83a, 83b of the clamping ring 8, and at the same time, the grooves 123a, 123b of the inner tube 120 engage the ribs 54a, 54b of the receiving part 5, as shown in FIG. 18c.

The cooperation of the engagement structures in the form of ribs and grooves connects the outer tube 110 to the clamping ring 8 and the inner tube 120 to the receiving part 5 in form-fit manners, respectively, such that a force for moving the clamping ring 8 relative to the receiving part 5 in an axial direction can be transmitted through the instrument 100.

FIGS. 19a to 20b illustrate the use of the instrument 100 for both locking of the head 3 and releasing the lock on the head 3 relative to the receiving part 5. In FIGS. 19a and 19b, the clamping ring 8 is in the upper position, where the upper end 8a abuts against a lower end 50a of the upper part 50 of the receiving part 5. The head 3 is pivotable in the head receiving portion 57, but cannot be pulled out through the opening at the lower end 5b. The receiving part 5 is held by the inner tube 120 in a form-fit manner, so that the receiving part 5 cannot move relative to the inner tube 120, at least in an axial direction. The clamping ring 8 is engaged by the outer tube 110. As can be seen in FIG. 19b the front end 120a of the inner tube 120 abuts against the shoulder 111a of the outer tube 110.

As can be seen further in the figures, an inner diameter of the inner tube 120 above the shoulder 122 is such that the fixation element 9 can be inserted through the inner tube 120 and into the upper part 50 of the receiving part 5.

In the next step, as depicted in FIGS. 20a and 20b, the outer tube 110 is moved downward relative to the inner tube 120, so that the clamping ring 8 is moved slightly downward relative to the receiving part 5, thereby compressing head receiving portion 57. As depicted in greater detail in FIG. 20b, the clamping ring 8 has moved downward away from the abutment of the upper part 50 of the receiving part 5 and the widening outer surface portion 57a of the head receiving portion 57 and the tapered inner surface portion 87 of the clamping ring 8 cooperate to generate an increasing pressure in a radial direction onto the head 3 and the pressure member 7. By means of this, the head 3 is locked in the receiving part 5 in its pivotal position by the instrument 100 acting onto the clamping ring 8. Meanwhile, the rod 6 is still movable to allow adjustments of the rod position relative to the receiving part 5. In this locking position of the clamping ring 8, as shown in FIGS. 20a and 20b, the instrument 100 can also be used to pull the bone anchoring device towards the inserted rod 6, to correct a position of the associated vertebra.

Next, for performing further adjustments, the lock on the head 3 can be released, where the outer tube 110 is pulled up relative to the inner tube 120, until the shoulder 111a abuts against the free end 120a of the inner tube 120. Thereby, the clamping ring 8 is moved upward out of the locking position and back into the open position, which is the same position depicted in FIGS. 19a and 19b.

With the possibility of locking the head 3, and then also of releasing the locked head 3, while the rod 6 and the fixation element 9 are already inserted in the receiving part 5, a greater variety of adjustment steps can be carried out, which simplifies the surgical procedure. For example, the polyaxial bone anchoring device together with the instrument 100 can be used in a similar manner as a polyaxial bone anchoring device with a two part fixation element that provides independent rod and head fixation, wherein, for example, an inner fixation element is used to fix the rod and an outer fixation element is used to lock the head independently from the locking of the rod.

In another manner of use, the polyaxial bone anchoring device can be used as a monoaxial bone anchoring device, in that the head 3 is locked relative to the receiving part 5 while adjustments to the rod positions can still be made.

As depicted in FIG. 21a, in the locking position of the clamping ring 8, the bone anchoring device can be pulled against the rod and the position of the vertebra can be corrected. Finally, as shown in FIG. 21b, once a correct angular position of the head 3 and a correct position of the receiving part 5 relative to the rod 6 has been found, the fixation element 9 can be tightened, for example, with a drive tool 300 that is inserted through the inner tube 120 and that engages the fixation element 9. Tightening of the fixation element 9 moves the rod 6 downwards, which in turn presses the rod 6 onto the rod support surface 78 of the pressure member 7 and locks the whole device. The instrument 100 can then be removed by rotating the instrument 100 so that the grooves 113a, 113b, 123a, 123b disengage from the ribs 83a, 83b, 54a, 54b and the legs of the instrument 100 are aligned with the rib-free surfaces 55a, 55b, 84a, 84b. In this position, the instrument 100 can be pulled away from the receiving part 5. The extended tabs at the first end 5a of the receiving part 5 may then be broken off at the end of the procedure.

In a surgical operation, a plurality of bone anchoring devices are connected by the rod 6. It may be possible to use several instruments 100, respectively, for several bone anchoring devices simultaneously, which facilitates the steps such as the adjustment, re-positioning, etc. of each bone anchoring device relative to the rod 6.

A further embodiment of a bone anchoring device and instrument is shown with respect to FIGS. 22 and 23. The embodiment according to FIGS. 22 and 23 differs from the previous embodiments only in the engagement structures for the instrument and the bone anchoring device. All other parts are the same or similar to the previously described embodiments, and are indicated with the same reference numerals as in the previous embodiments, and their descriptions therefore will not be repeated. The receiving part 5' has grooves 154a, 154b at an outer wall of each of the legs 52a, 52b. The circumferentially extending grooves 154a, 154b are located at a distance from the groove 5c that provides the break-off section. The instrument 100' has corresponding circumferential ribs 133a, 133b at an inner wall of the inner tube 120. The ribs 133a, 133b are at a position and are shaped so as to be able to engage the grooves 154a, 154b of the receiving part 5'. The function and operation of the parts may be the same as similar to that of the previously described embodiments. For engaging the receiving part 5' with the instrument 100', the legs of the instrument 100' have to be spread when placing the instrument 100' over the receiving part 5'.

A further modified embodiment of the instrument, which facilitates easier outward splaying of the legs is depicted in FIG. 24. Like numerals denote the same or similar parts as in the previous embodiments. In the instrument 100" shown in FIG. 24, the outer tube 110 and the inner tube 120 are both provided with slots 200a, 200b, which allow the legs to spread apart more easily when the instrument 100" is moved downward relative to the bone anchoring device, similarly as shown in FIGS. 18b and 18c. The circumferential ribs 133a, 133b may thus more easily slide over the outer surface of the receiving part 5' and snap into or otherwise engage the corresponding grooves 154a, 154b. Depending on the particular design of the instrument 100" and/or the bone anchoring device, a further rotation step for engaging the respective parts may or may not be necessary.

Further modifications can also be contemplated. For example, on each of the receiving part and/or the clamping ring, any different combination of ribs and grooves can be provided, and the instrument may have a counterpart or complementary structure, in other words, a combination of grooves and ribs configured to engage the structures at the receiving part. The shape and the number of the engagement elements may also vary. One single engagement element on the receiving part and the clamping ring may be sufficient in some embodiments. The ribs and grooves need not extend circumferentially in a plane in some embodiments, but can instead extend along a helix-shape, for example. Therefore, the engagement structures on the instrument, the receiving part, and the clamping ring can also be realized with, for example, threads. Other engagement structures may also be contemplated that provide a form-fit connection which can transmit forces onto the bone anchoring device and which can be affected by a rotating and/or sliding movement of the instrument relative to the bone anchoring device. In some embodiments, the engagement structures may also be provided on only one side of the receiving part and on one side of the clamping ring. The position of the engagement structures may be different from that shown in the embodiments above.

The bone anchoring device according to other embodiments of the invention can be provided in still further modified forms. For example, the head of the bone anchoring element can have any other shape, such as, for example, a cylindrical shape, or a spherical shape with flattened sides, wherein a monoplanar device is provided that allows pivoting of the bone anchoring element in a single plane. The head can also be conically shaped or otherwise shaped, where the internal hollow section of the head receiving portion can be adapted to the specific shape. In a further modification, the flexibility of the head receiving portion may be based on or facilitated by properties of the material, for example, a plastic material may be used, and the slits in the head receiving portion may be fully or partly omitted.

In the pressure member, the upstanding legs may be omitted. Other structures may be provided that prevent the pressure member from escaping out of the receiving part during insertion of the head. The pressure member may also be shaped such that it can be inserted from the lower end of the receiving part.

In some embodiments, the head receiving portion can have an inclined open end or can be otherwise asymmetric to allow for a greater angulation of an inserted head in one direction.

The outer surface of the head receiving portion and the inner surface of the clamping ring can also have various other shapes that result in compression of the head receiving portion by the clamping ring when the clamping ring is shifted downward. Also, the clamping ring can have various other designs.

The alignment features such as the flat portions can have any other shape or can be omitted. Only one alignment feature may be provided in some embodiments. The projections and the recesses for securing the rotational position of the clamping ring relative to the receiving part can also have any other shape. There can be more or less than one projection or recess. The recess may be present at the clamping ring and the projection at the receiving part. The rotational securing structure can also be omitted.

The extended tabs on the receiving part can be omitted. In addition, in some embodiments, other kinds of fixation elements can also be used, for example, non-threaded locking elements that have an alternative advancement structure. In addition, all kinds of bone anchoring devices can be used, such as, for example, nails or bone anchors with barbs.

Meanwhile, the use of the instrument has been shown in connection with a bone anchoring element that has already been inserted into the bone. The bone anchoring element may also be pre-assembled with the receiving part. In this case, the bone anchoring device can be a top-loading polyaxial bone anchoring device in some embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchoring device comprising:
a receiving part for coupling a rod to a bone anchoring element, the receiving part comprising a first end, a second end below the first end, a central axis extending between the first end and the second end, a recess at the first end for receiving the rod, and a head receiving portion defining an accommodation space at the second end for pivotably holding a head of the bone anchoring element, the head receiving portion being at least partially flexible;
a pressure member positionable in the receiving part and configured to exert pressure on the head when the head is held in the head receiving portion of the receiving part; and
a clamping ring positionable around the head receiving portion for locking an inserted head relative to the receiving part, wherein when the clamping ring is around the head receiving portion and when the accommodation space is vacant, the clamping ring is movable from a first position to a second position to increase a radial force exerted by the clamping ring onto the head receiving portion;
wherein when the clamping ring is at the first position, a portion of the clamping ring abuts a portion of the receiving part to restrict movement of the clamping ring towards the first end of the receiving part, while a surface of the clamping ring that faces upwards towards the first end of the receiving part is exposed to an outside of the bone anchoring device for engaging an instrument to move the clamping ring to the second position.

2. The bone anchoring device of claim 1, wherein the receiving part comprises a first engagement structure comprising a surface that faces downwards towards the second end of the receiving part and the clamping ring comprises a second engagement structure comprising the surface that faces upwards towards the first end of the receiving part, and wherein the first engagement structure and the second engagement structure are configured to be engaged by the instrument to transmit a force via the instrument onto the clamping ring and onto the receiving part, such that the clamping ring and the receiving part can be moved relative to each other along the central axis.

3. The bone anchoring device of claim 2, wherein the first engagement structure and the second engagement structure are arranged at an outer circumferential surface of the receiving part and at an outer circumferential surface of the clamping ring, respectively.

4. The bone anchoring device of claim 3, wherein the first engagement structure extends farther radially outwardly than all other portions of the receiving part.

5. The bone anchoring device of claim 3, wherein the second engagement structure extends farther radially outwardly than all other portions of the clamping ring.

6. The bone anchoring device of claim 2, wherein the first engagement structure is arranged at a distance from the first end of the receiving part.

7. The bone anchoring device of claim 2, wherein the first engagement structure and the second engagement structure is each arranged asymmetric with respect to a plane extending through the central axis of the receiving part and through a longitudinal axis of the recess.

8. The bone anchoring device of claim 2, wherein the first engagement structure and the second engagement structure are engageable with the instrument through rotating the instrument around the central axis.

9. The bone anchoring device of claim 2, wherein the first engagement structure and the second engagement structure each comprises at least one circumferentially extending rib or at least one circumferentially extending groove.

10. A system comprising the bone anchoring device of claim 2 and an instrument comprising:
   an outer tube having a third engagement structure comprising a surface that faces downwards towards the second end of the receiving part when the instrument is connected to the bone anchoring device for engaging the second engagement structure of the clamping ring; and
   an inner tube positioned at least partially in the outer tube, the inner tube having a fourth engagement structure comprising a surface that faces upwards towards the first end of the receiving part when the instrument is connected to the bone anchoring device for engaging the first engagement structure of the receiving part;
   wherein the inner tube is axially displaceable relative to the outer tube, such that when the third engagement structure of the outer tube engages the second engagement structure of the clamping ring and the fourth engagement structure of the inner tube engages the first engagement structure of the receiving part, the axial displacement of the inner tube relative to the outer tube is configured to move the clamping ring relative to the receiving part.

11. The system of claim 10, wherein the inner tube and the outer tube each defines a recess extending from a front end towards an opposite end for passing a rod therethrough, and wherein the recess has an inverted U-shape and forms two free legs at the front end of each of the inner tube and the outer tube.

12. The bone anchoring device of claim 1, wherein the head receiving portion comprises a tapered outer surface portion.

13. The bone anchoring device of claim 12, wherein the clamping ring comprises a tapered inner surface portion that cooperates with the tapered outer surface portion of the head receiving portion.

14. The bone anchoring device of claim 1, wherein the head receiving portion comprises a narrowing inner surface portion at the second end.

15. The bone anchoring device of claim 14, wherein the pressure member comprises a narrowing outer surface portion that cooperates with the narrowing inner surface portion of the head receiving portion.

16. The bone anchoring device of claim 1, wherein when the clamping ring is around the head receiving portion, the clamping ring is secured against rotation relative to the receiving part.

17. A bone anchoring device comprising:
   a bone anchoring element comprising a shank for anchoring to bone and a head;
   a receiving part for coupling a rod to the bone anchoring element, the receiving part comprising a first end, a second end, a central axis extending between the first end and the second end, a recess at the first end for receiving the rod, and a head receiving portion at the second end for pivotably holding the head, the head receiving portion being at least partially flexible;
   a pressure member positionable in the receiving part and configured to exert pressure on the head when the head is held in the head receiving portion of the receiving part; and
   a clamping ring positionable around the head receiving portion;
   wherein when the clamping ring is around the head receiving portion, the head is insertable into the head receiving portion, and the clamping ring is movable from a first position wherein the inserted head is pivotable relative to the receiving part for changing an angular position of the receiving part relative to the bone anchoring element, to a second position wherein the clamping ring exerts a radial force onto the head receiving portion to lock the angular position of the receiving part relative to the bone anchoring element while the recess for the rod remains vacant or unobstructed.

18. The bone anchoring device of claim 17, wherein the head of the bone anchoring element is insertable into the receiving part from the second end.

19. The bone anchoring device of claim 18, wherein the pressure member can assume an insertion position in the receiving part where the pressure member is secured against falling out of the receiving part when the head is inserted into the receiving part.

20. The bone anchoring device of claim 17, wherein the pressure member comprises a flexible portion that is configured to at least partially surround the head and to be compressed to lock the head when the clamping ring is at the second position.

21. A method for coupling a rod to a bone via a bone anchoring device comprising a bone anchoring element comprising a shank for anchoring to bone and a head, a receiving part comprising a first end, a second end, a central axis extending between the first end and the second end, a recess at the first end for receiving the rod, and a head receiving portion at the second end for pivotably holding the head, the head receiving portion being at least partially flexible, a pressure member positionable in the receiving part and configured to exert pressure on the head when the head is held in the head receiving portion of the receiving part, a clamping ring positionable around the head receiving portion, wherein when the clamping ring is around the head receiving portion, the head is insertable into the head receiving portion, and a fixation element, the method comprising:
   inserting the shank of the bone anchoring element into bone;
   pivoting and changing an angular position of the receiving part relative to the bone anchoring element when the head is in the head receiving portion and the clamping ring is around the head receiving portion at a first position;

moving the clamping ring from the first position to a second position wherein the clamping ring exerts a radial force onto the head receiving portion to lock the angular position of the receiving part relative to the bone anchoring element while the recess at the first end remains vacant or unobstructed or while the rod is in and remains movable in the recess; and urging the rod axially in the recess towards the head with the fixation element to finally lock the rod and the head relative to the receiving part.

22. The method of claim 21, further comprising:

moving the clamping ring from the second position back to the first position to unlock the head relative to the receiving part;

pivoting the receiving part relative to the bone anchoring element to readjust the angular position of the receiving part relative to the bone anchoring element; and moving the clamping ring from the first position back to the second position to lock the angular position of the receiving part relative to the bone anchoring element.

23. A bone anchoring device comprising:

a bone anchoring element comprising a shank for anchoring to bone and a head;

a receiving part for coupling a rod to the bone anchoring element, the receiving part comprising a first end, a second end below the first end, a central axis extending between the first end and the second end, a recess at the first end for receiving the rod, and a head receiving portion at the second end for pivotably holding the head, the head receiving portion being at least partially flexible;

a pressure member positionable in the receiving part and configured to exert pressure on the head when the head is held in the head receiving portion of the receiving part; and a clamping ring positionable around the head receiving portion;

wherein when the clamping ring is around the head receiving portion, the head is insertable from the second end of the receiving part into the head receiving portion, and the clamping ring is movable from a first position wherein the inserted head is pivotable relative to the receiving part, to a second position wherein the clamping ring exerts a radial force onto the head receiving portion to lock the inserted head relative to the receiving part; and wherein the receiving part comprises a first engagement surface that faces downwards towards the second end of the receiving part and the clamping ring comprises a second engagement surface that faces upwards towards the first end of the receiving part, and wherein the first and second engagement surfaces are configured to be engaged by an instrument to transmit a force via the instrument onto the clamping ring and onto the receiving part, such that the clamping ring and the receiving part can be moved relative to each other along the central axis.

* * * * *